United States Patent [19]

Drucker et al.

[11] 4,368,184
[45] Jan. 11, 1983

[54] METHOD FOR THE APPLICATION OF ANTIPERSPIRANT POWDER COMPOSITIONS

[75] Inventors: Jacob Drucker, Holmdel; Frank Shea, Cranbury, both of N.J.

[73] Assignee: Carter-Wallace, Inc., New York, N.Y.

[21] Appl. No.: 169,160

[22] Filed: Jul. 15, 1980

Related U.S. Application Data

[63] Continuation-in-part of Ser. No. 853,097, Nov. 21, 1977, abandoned.

[51] Int. Cl.³ .................. A61K 7/34; A45D 33/12
[52] U.S. Cl. ...................... 424/66; 29/120; 222/414; 401/200; 401/215
[58] Field of Search ............ 401/215, 216, 197, 200, 401/209, 210, 211, 213, 214, 217, 208, 219; 222/414; 29/120; 424/65, 66

[56] References Cited

U.S. PATENT DOCUMENTS

| | | | |
|---|---|---|---|
| 1,776,981 | 9/1930 | Rae | 401/208 |
| 2,643,798 | 6/1953 | Neff | 222/414 |
| 3,166,618 | 1/1965 | Fehling | 264/242 |
| 3,870,775 | 3/1975 | Castro | 264/DIG. 53 |
| 4,037,977 | 7/1977 | Ronai | 401/209 |
| 4,239,017 | 12/1980 | Schwarz | 29/120 |

FOREIGN PATENT DOCUMENTS

| | | | |
|---|---|---|---|
| 422306 | 6/1947 | Italy | 401/209 |
| 399621 | 10/1933 | United Kingdom | 401/208 |

*Primary Examiner*—Clyde I. Coughenour
*Attorney, Agent, or Firm*—Kevin B. Clarke

[57] ABSTRACT

Method for applying loose, free-flowing powder compositions to the skin from a dispensing container utilizing a dispensing ball or roller containing filamentous hair-like projections over its exterior surface, and dry antiperspirant powder compositions based on particulate aluminum and/or zirconium chlorohydrate as the active antiperspirant ingredient including minor amounts of a surfactant vehicle to aid in maintaining the powder on the skin after contact therewith.

4 Claims, 1 Drawing Figure

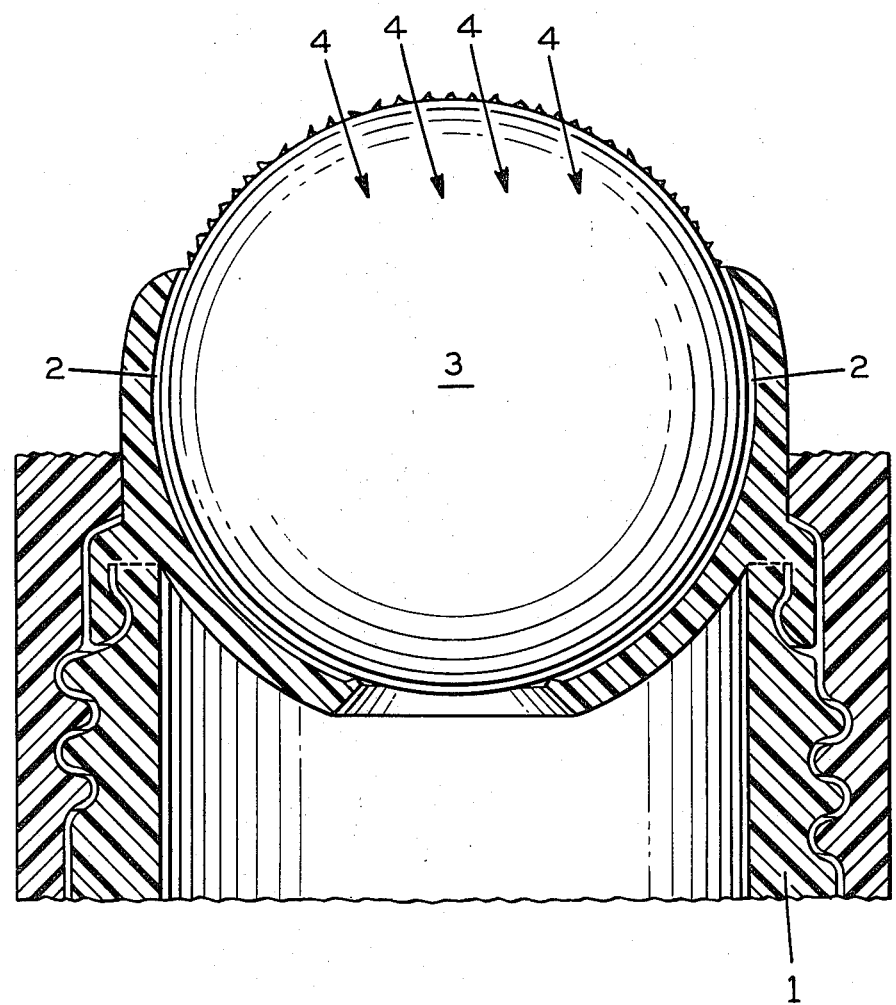

METHOD FOR THE APPLICATION OF ANTIPERSPIRANT POWDER COMPOSITIONS

This application is a continuation-in-part of copending application Ser. No. 853,097 filed Nov. 21, 1977 now abandoned.

This invention relates to the application of powder preparations to the body. More particularly, the invention relates to powder antiperspirant compositions and their application to the body.

Antiperspirant products which are used to inhibit perspiration are generally sold in the form of aerosol sprays, gel or wax sticks, liquid roll-ons, creams, compact powders, and the like. It has been additionally proposed to provide antiperspirant preparations in dry loose powder form. However, loose powder antiperspirants, usually applied with a puff or from a squeeze bottle, are messy to use and have the disadvantage that the loose powder "dusts," or "blooms" which causes the antiperspirant particles to become airborne and in some cases may be inhaled and may cause discomfort to the user.

Further, considerable difficulty has been experienced in the past in applying and maintaining powdered antiperspirants satisfactorily on the skin in sufficient quantity so as to obtain the desired efficacy.

We have now found that loose, free-flowing powder antiperspirant compositions can be dispensed from ball or roller top containers in amounts which are adequate to effectively inhibit perspiration.

A principle aspect of the present invention is to provide an antiperspirant package containing loose, free-flowing powder antiperspirant formulations such as described in detail hereinafter, together with a ball-top or roller-top container adapted to dispense a loose-powder formulation. The novel method of application of the present invention is achieved by providing a container such as a bottle, having an open end, a generally spherical or cylindrical, comparatively rough-surfaced or textured polyethylene, polypropylene or polystyrene dispensing ball or roller adapted to fit partially within the open end of the container, means for rotatably supporting the ball or roller partially within the open end of the container which cooperates with the dispensing ball or roller to retain it in assembly on a container and to provide a seal against leakage of the contents when the container is not in use.

A particular aspect of the package employed in the present invention is to provide a dispensing ball or roller wherein the ball or roller surface contains filamentous structures that resemble hair-like projections on the outside circumference of the ball or roller and which permit a ball or roller adhering layer of the loose, free-flowing antiperspirant formulation to be applied to the body surface by a rolling movement of the ball or roller along such surface.

The desired texture or finish on the ball or roller may be achieved in any one of several ways.

In the case of ball-type dispensers, the balls are conventionally polished by tumbling in a material such as pumice for periods of time ranging from about one to several hours. Generally, the longer the polishing operation is performed, the smoother and less textured is the surface of the ball produced. Accordingly, for purposes of the present invention, the polishing of the balls may be substantially curtailed or eliminated in order to obtain balls having the desired surface texture.

Alternatively, the balls or rollers may be mechanically scored or grooved or impressed with various patterns after manufacture.

In the drawing, the figure is a fragmentary section showing the preferred applicator of the present invention including a ball holder 1 which is generally cylindrical in form with the upper portion of said cylinder having its interior surface 2 shaped to conform to the curvature of a portion of the applicator ball 3 and of such axial extent as to enclose a major portion of the ball. The ball 3 contains filamentous structures 4, that resemble hair-like projections, on its exterior surface.

We have found that the amount and length or size of the filamentous, hair-like projections on the exterior surface of the ball or roller are controlling factors in the performance; i.e., product delivery, of the packages of this invention.

The ball applicator preferred for use in the present invention may vary in size from a diameter of less than about one inch to a diameter of more than about two inches. The total number of filamentous, hair-like projections on the ball surface can vary on the order of from about 1000 to about 4000 per square inch of surface area, preferrably between 2500 and 3000 projections per square inch. The filamentous, hair-like projections may vary in length up to about 0.01 inches preferrably about 0.00009 inches to about 0.007 inches.

Since dry powdered astringent materials applied to the human skin do not always adhere satisfactorily to it, a vehicle is often present with the finely divided astringent powder so as to hold to it and to help maintain the powder on the skin after contact therewith. Such vehicles have usually been lipophilic materials which exhibit very little water solubility. Many of such materials can insulate the aluminum chlorhydrate from contact with moisture on the skin and thereby delay the onset of astringent action. It is desirable to accelerate the dissolving of aluminum chlorhydrate, rather than to delay this action. Yet, it remains important to hold the powdered aluminum chlorhydrate onto the skin.

In U.S. Pat. No. 3,324,004, it has been proposed to prepare dry powder antiperspirants in compact powder form by adding aluminum chlorhydrate to customary components of a face powder together with mineral oil, water and a lauryl alcohol polyoxyethylene ether surfactant with the latter being present to suppress the hygroscopicity of the aluminum chlorhydrate metallic salts. Such compact powders are not suitable for dispensing from roller or ball-top containers which require loose free-flowing powders.

As another aspect of the present invention, there are provided loose, free-flowing powder compositions suitable for use in ball-top or roller-top containers for the roll-on application of a dry powder antiperspirant which adheres well to the skin and which consists essentially of an aluminum and/or zirconium based astringent in proportions sufficient to have an effective antiperspirant action, minor amounts of a lauryl alcohol polyoxyethylene ether characterized by the presence of about 4 ethylene oxide units; a binding agent such as lower an aliphatic ester of a higher fatty acid, such as isopropyl myristate, isopropyl palmitate, etc.; a pyrogenic colloidal silica, having particle sizes in the 0.1 to 2 micron range; water, and, if desired, perfume together with major amounts of bulking agents or fillers such as corn starch, talc, protein flours, dyes and the like.

Aluminum chlorhydrate, having the formula $Al_2(OH)_5Cl \cdot 2H_2O$, is a standard article of commerce and long with the aluminum/zirconium complexes is available in finely divided powdered form suitable for dispensing from a roll-top dispenser. For the present applications, particles of astringent salt will be small usually of about 1 to 1,000 microns, preferably 2 to 100 microns and most preferably averaging about 10 to 50 microns in diameter. It is also within the contemplation of the present invention to include minor amounts of aluminum chloride in combination with the aluminum chlorhydrate and/or zirconium astringent.

The lauryl alcohol polyoxyethylene ether is obtainable by condensing lauryl alcohol with 4 mols of ethylene oxide. Accordingly, its chemical constitution is: $C_{12}H_{25}O(CH_2CH_2O)_4OH$. It is available commercially as "Brij 30," a product of Atlas Chemical Industries.

The finely divided silica is present to assist in maintaining a uniform coating of the astringent particles on the skin and to absorb any excess perspiration not taken up by the astringent particles; yet, it releases such perspiration to the astringent to promote activation thereof. For best results, the finely divided silica is a colloidal silica, preferably a pyrogenic type, having a particle size in the 0.1 to 10 micron range, preferably of 0.1 to 2 microns. Such products are available under the tradename Cab-O-Sil, such as Cab-O-Sil M-5, a product of Cabot Corporation. Of course, equivalent materials having similar properties may be employed.

The binder to be employed in the powder product can be any anhydrous material commonly used in antiperspirant formulations such as mineral oil, lanolin and preferably, a lower aliphatic ester of a higher fatty acid such as isopropyl myristate or isopropyl palmitate.

The bulking agent or filler comprises in excess of 50% by weight of the total compositions, generally from about 50.01% to about 66.67% by weight of the total composition.

The astringent aluminum chlorohydrate and/or zirconium complex, either alone or in combination with up to about 2% by weight of aluminum chloride, is present in an amount of from about 20% to about 45% by weight.

The finely divided silica is present in an amount of from about 0.5% to about 2.5% by weight.

The lauryl alcohol polyoxyethylene ether may be present in an amount of from about 0.5% to about 1.5% by weight, preferably 1% by weight.

The water and perfume are optional and are present in minor amounts of from about 0.5% to about 1.5% by weight.

The following are non-limiting examples of the novel loose powder antiperspirants of the present invention. The ingredients are blended together in conventional fashion.

EXAMPLE I

| Ingredient | % W/W |
|---|---|
| Aluminum chlorohydrate | 32.00 |
| Cab-O-Sil M-5 (silica) | 3.00 |
| Corn Starch | 10.00 |
| Isopropyl palmitate | 4.25 |
| Perfume Noville #10430 | 0.75 |
| Talc | 50.00 |
| | 100.00 |

EXAMPLE II

| Ingredient | % W/W |
|---|---|
| Talc | 66.75 |
| Cab-O-Sil M-5 (silica) | 1.50 |
| Isopropyl palmitate | 4.00 |
| Perfume, Noville #18430 | 0.75 |
| Aluminum chloride | 0.50 |
| Water | 0.50 |
| Aluminum chlorohydrate | 25.00 |
| Brij 30 SP (Laureth-4) | 1.00 |
| | 100.00 |

EXAMPLE III

| Ingredient | % W/W |
|---|---|
| Aluminum dichlorohyrate | 40.00 |
| Tween 20 (polysorbate 20) | 1.00 |
| Brij 30 SP (Laureth-4) | 1.00 |
| Fragrance Noville #18430 | 0.75 |
| Talc | 50.75 |
| Cab-O-Sil M-5 (silica) | 1.50 |
| Aluminum chloride | 1.00 |
| Water | 1.00 |
| Isopropyl Palmitate | 3.00 |
| | 100.00 |

EXAMPLE IV

| Ingredient | % W/W |
|---|---|
| Talc | 65.75 |
| Cab-O-Sil M-5 (Silica) | 1.50 |
| Isopropyl palmitate | 4.00 |
| Perfume, Noville #18430 | 0.75 |
| Aluminum chloride | 1.00 |
| Water | 1.00 |
| Aluminum chlorohydrate | 25.00 |
| Brij 30 SP (Laureth-4) | 1.00 |
| | 100.00 |

EXAMPLE V

| Ingredient | % W/W |
|---|---|
| Aluminum chlorohydrate | 40.00 |
| Tween 20 (Polysorbate 20) | 1.00 |
| Brij 30 SP (Laureth-4) | 1.00 |
| Fragrance Noville #8430 | 0.75 |
| Talc | 50.75 |
| Cab-O-Sil M-5 (Silica) | 1.50 |
| Aluminum chloride | 1.00 |
| Water | 1.00 |
| Isopropyl palmitate | 3.00 |
| | 100.00 |

EXAMPLE VI

| Ingredient | % W/W |
|---|---|
| Aluminum zirconium chlorohydrate complex | 40.00 |
| Tween 20 (Polysorbate 20) | 1.00 |
| Brij 30 SP (Laureth-4) | 1.00 |
| Fragrance Noville #18430 | 0.75 |
| Talc | 50.75 |
| Cal-O-Sil M-5 (Silica) | 1.50 |
| Aluminum chloride | 1.00 |
| Water | 1.00 |

-continued

| Ingredient | % W/W |
|---|---|
| Isopropyl Palmitate | 3.00 |
| | 100.00 |

In order to demonstrate the effectiveness of application according to the method of the present invention, product delivery tests were conducted on three different types of polyethylene balls having a diameter of 0.995", namely a smooth non-filamentous ball (estimated density of projections 78.8/in.$^2$, a dense filamentous ball (estimated density of projections 5,423/in.$^2$) and the preferred ball (standard ball) of the present invention (estimated density of projections 2,884/in.$^2$).

Product delivery tests were conducted on the three different types of balls wherein the amount of product delivered is measured by weight after application over a controlled area. The data collected is set forth in Table I following:

TABLE I

| | PRODUCT DELIVERY | | |
|---|---|---|---|
| | Smooth Ball | Dense Ball | Standard Ball |
| 1. | 0.01 gm | 0.27 gm | 0.15 gm |
| 2. | .02 | .30 | .13 |
| 3. | .01 | .28 | .10 |
| 4. | .02 | .34 | .12 |
| 5. | .01 | .26 | .15 |
| 6. | .02 | .31 | .12 |
| 7. | .02 | .31 | .11 |
| 8. | .02 | .29 | .12 |
| 9. | .01 | .38 | .11 |
| 10. | .01 | .33 | .11 |
| 11. | .01 | .28 | .15 |
| 12. | .02 | .35 | .11 |
| 13. | .02 | .26 | .11 |
| 14. | .01 | .35 | .10 |
| 15. | .01 | .30 | .11 |
| means = | 0.0147 gm | 0.307 gm | 0.120 gm |

Projection size and density in the foregoing tests were determined by taking representative micrographs, of the three ball variations under test, with a Nikon Optical Projector 20X and transmitted light. From these micrographs measurements were taken of all projections in focus. Each micrograph represented an area of 0.260×0.020 inches. Results of the data collected were as follows:

| Non-filamentous balls | | Samples = 10 | |
|---|---|---|---|
| Total projections | 41 | | |
| Mean Length | 0.0017" | Range 0.0005 to 0.00063 | |
| Dense-filamentous balls | | Samples = 10 | |
| Total projections | 282 | | |
| Mean Length | 0.0052" | Range 0.0007 to 0.0205 | |
| Standard balls | | Samples = 10 | |
| Total projections | 150 | | |
| Mean Length | 0.00022 | Range 0.0008 to 0.0063 | |

The density of projections was determined by taking the number totals from each 20X micrograph and using the following calculation:

Surface area of a sphere $= 4\pi r^2$

Area of measured section $Am = 0.260'' \times 0.020'' = 0.0052$ in.$^2$

Area of ball $$Ar = 4\pi \frac{(0.995)^2}{2} = \frac{12.441 \text{ in}^2}{4} = 3.11 \text{ in.}^2$$

Proportion of area of ball measured $$\% P = \frac{0.0052 \times 100}{\frac{12.44}{4}} = 0.1672\% = \frac{1}{598}$$

| | Average No. Projections/Am | Calculated No. Projections/Ar | Estimated density/in$^2$ |
|---|---|---|---|
| Non-filamentous | 0.41 | 245 | 78.8 |
| Dense filamentous | 28.2 | 16,864 | 5423 |
| Standard | 15.0 | 8,970 | 2884 |

The foregoing data demonstrates that the number or density of projections on the ball surface is a controlling factor in the performance or product delivery rate of the ball. Smooth balls (78.8 projections/in.$^2$) do not deliver adequate amounts of product. Dense balls (5,423 projections/in.$^2$) deliver excessive amounts of products. The standard ball of this invention (2,884 projections/in.$^2$) performs within the accepted delivery rates for antiperspirant compositions.

It was also found that the size or length of the filamentous projections plays an important part in efficient product delivery. It was noted that dense samples which had a mean length of 0.0052 and a range as high as 0.0205 incurred binding and clogging problems during application. This problem is eliminated by maintaining the length of the filamentous projection at 0.010" or lower.

The invention in its broader aspects is not limited to the specific compositions, steps, methods, combinations and improvements described, but departures may be made therefrom within the scope of the accompanying claims without departing from the principles of the invention and without sacrificing its principal advantages.

What is claimed is:

1. A method for applying loose, free-flowing antiperspirant powder compositions to the skin which comprises dispensing a loose, free-flowing powder from a ball-top container adapted to dispense said loose, free-flowing powder to the body surface by rolling movement of the ball or roller along such surface, wherein said container is a dispenser having an open end, a generally spherical or cylindrical, comparatively rough-surfaced or textured dispensing ball or roller, wherein said surface contains filamentous structures in a density of 1000 to about 4000/in$^2$ and from about 0.007 to about 0.01 inches in length, adapted to fit partially within the open end of the container, means for rotatably supporting the ball partially within the open end of the container which cooperates with the dispensing ball or roller to retain it in assembly on the dispenser.

2. A method according to claim 1 wherein said dispenser is a cylindrical roller-type dispenser containing filamentous structures on the roller surface.

3. A method according to claim 1 wherein said loose, free-flowing powder composition comprises from about 20% to about 45% by weight of an astringent selected from the group comprising aluminum and zirconium based compounds, from about 50% to about 66.67% by weight of a bulking agent, from about 2.5% to about 4% by weight of an anhydrous binder material, from about 0.5% to about 2.5% by weight finely divided silica and up to about 1.5% by weight water.

4. A method according to claim 3 wherein said loose, free-flowing powder antiperspirant includes from about 0.5% to about 1.5% by weight of a lauryl alcohol polyoxyethylene ester.

* * * * *